(12) United States Patent
Sainz-Nieto

(10) Patent No.: US 12,406,336 B1
(45) Date of Patent: *Sep. 2, 2025

(54) SYSTEMS AND METHODS FOR ENHANCING ULTRASOUND IMAGES USING ARTIFICIAL INTELLIGENCE

(71) Applicant: Andrew Sainz-Nieto, Woodstock (CA)

(72) Inventor: Andrew Sainz-Nieto, Woodstock (CA)

(73) Assignee: MILLER AND COMPANY IP HOLDINGS (PA)

( * ) Notice: Subject to any disclaimer, the term of this patent is extended or adjusted under 35 U.S.C. 154(b) by 0 days.

This patent is subject to a terminal disclaimer.

(21) Appl. No.: 18/406,879

(22) Filed: Jan. 8, 2024

(51) Int. Cl.
| | | |
|---|---|---|
| *G06T 5/00* | (2024.01) | |
| *G06T 3/40* | (2006.01) | |
| *G06T 5/60* | (2024.01) | |
| *G16H 10/60* | (2018.01) | |

(52) U.S. Cl.
CPC .............. *G06T 5/60* (2024.01); *G06T 3/40* (2013.01); *G16H 10/60* (2018.01); *G06T 2207/10016* (2013.01); *G06T 2207/10132* (2013.01); *G06T 2207/20081* (2013.01); *G06T 2207/20084* (2013.01); *G06T 2207/30044* (2013.01); *G06T 2207/30201* (2013.01)

(58) Field of Classification Search
CPC ... G06T 5/60; G06T 3/40; G06T 2207/10016; G06T 2207/10132; G06T 2207/20081; G06T 2207/20084; G06T 2207/30044; G06T 2207/30201; G16H 10/60
See application file for complete search history.

(56) References Cited

U.S. PATENT DOCUMENTS

| | | | |
|---|---|---|---|
| 11,875,507 B1 * | 1/2024 | Gardella | G06T 7/269 |
| 2019/0295223 A1 * | 9/2019 | Shen | G06T 5/60 |
| 2023/0394628 A1 * | 12/2023 | Lee | G06V 10/7715 |
| 2023/0419721 A1 * | 12/2023 | Lee | G06T 5/70 |
| 2024/0074726 A1 * | 3/2024 | Kim | A61B 8/4488 |

* cited by examiner

*Primary Examiner* — Khai M Nguyen

(57) ABSTRACT

Systems and methods are described for an artificial intelligence (AI)-based imaging system for generating an enhanced image and/or video of a fetus. The methods may comprise receiving at least one image of a fetus comprising pixel data of at least a portion of a face of the fetus. The method may further comprise generating, by an image enhancement model based on one or more facial features of the fetus, a graphically enhanced image of the fetus comprising a new image with at least one modified feature selected from the one or more facial features of the fetus, the modified feature causing pixel data of the image of the fetus to be enhanced compared to the at least one image of the fetus as originally received. The method may further comprise rendering, on a display screen of a user computing device, the graphically enhanced image depicting the enhanced pixel data.

21 Claims, 9 Drawing Sheets

SYSTEMS AND METHODS FOR ENHANCING ULTRASOUND IMAGES USING ARTIFICIAL INTELLIGENCE

FIELD OF THE DISCLOSURE

The present disclosure generally relates methods and apparatus for using artificial intelligence (AI) techniques to enhance images.

BACKGROUND

Ultrasound imaging is commonly used for aiding disease diagnosis and treatment, and a common use case is the non-invasive observation of fetuses during pregnancy. However, ultrasound images often have low contrast, therefore details in darker regions are often not perceptible. Moreover, ultrasound images and videos often lack clarity and visual appeal.

For the foregoing reasons, there is a need for systems and methods for generating an enhanced image and/or video of a fetus using artificial intelligence. The systems and methods disclosed herein may provide solutions to these problems and may provide solutions to other drawbacks of conventional techniques.

BRIEF SUMMARY

Generally, as described herein, systems and methods are described for generating an enhanced image and/or video of a fetus using artificial intelligence. Such systems and methods provide a remote (app-based) solution for individuals (users) to enhance the appearance of a fetus as captured by an image (e.g., digital images, video frames, etc.). For example, the systems and methods described herein may be used to efficiently receive an image of a fetus and generate a graphically enhanced lifelike image of the fetus. In some aspects, the systems and methods described herein may be used to provide image enhancement according to a tokenizer prompt as indicated by a user. In some aspects, the systems and methods described herein may be used to provide image enhancement of an image comprising a plurality of fetuses. In some aspects, the systems and methods described herein may be used to provide local image enhancement of an image comprising a plurality of fetuses.

The AI-based imaging systems and methods described herein may be implemented on one or more processors, either of a user computing device (e.g., such as one or more processors of a mobile device), and/or one or more processors of an imaging server or computer.

In one example aspect, an imaging application (app) may be downloaded or installed on a user computing device, such as an APPLE IPHONE or GOOGLE ANDORID phone through the APPLE APP store or GOOGLE PLAY store, respectively. A user may open the app to create a user profile. Creation of the profile may include a user providing or selecting preferences, such as allowing permissions for image(s) and/or data of the user to be obtained by the app via the computing device. In addition, creation of a profile may involve the user allowing permissions for the imaging app to be communicatively coupled to electronic health record app(s) of the user via the computing device.

More specifically, as described herein, an AI-based imaging system is disclosed. The AI-based imaging method comprises an imaging server comprising a server processor and a server memory. The system may further comprise an imaging application (app) configured to execute on a user computing device comprising a device processor and a device memory. The imaging app may be communicatively coupled to the imaging server. The system may further comprise an image enhancement AI model trained with pixel data of a plurality of training images of fetuses. The image enhancement AI model may be configured to output respective graphically enhanced images of the fetuses. Each graphically enhanced image may have at least one image feature modified compared to an original image. The system may further comprise computing instructions configured to execute on the server processor or the device processor. The computing instructions may cause the server processor or the device processor to receive at least one image of a fetus. The at least one image may comprise pixel data of at least a portion of a face of the fetus. The computing instructions may further cause the server processor or the device processor to generate, by the image enhancement model based on one or more facial features of the fetus, a graphically enhanced image of the fetus. The graphically enhanced image of the fetus may comprise a new image with at least one modified feature selected from the one or more facial features of the fetus. The modified feature may cause pixel data of the image of the fetus to be enhanced or altered compared to the at least one image of the fetus as originally received. The computing instructions may further cause the server processor or the device processor to render, on a display screen of the user computing device, the graphically enhanced image. The graphically enhanced image may depict the enhanced or altered pixel data.

In addition, as described herein, an AI-based imaging method is disclosed. The AI-based imaging method comprises receiving, at an imaging server comprising a server processor and a server memory, at least one image of a fetus. The at least one image may comprise pixel data of at least a portion of a face of the fetus. The AI-based imaging method further comprises generating, by an image enhancement AI model based on one or more facial features of the fetus, a graphically enhanced image of the fetus. The image enhancement AI model may be trained with pixel data of a plurality of training images of fetuses. The image enhancement AI model may be configured to output respective graphically enhanced images of the fetuses, each graphically enhanced image having at least one image feature modified compared to an original image. The graphically enhanced image of the fetus may comprise a new image with at least one modified feature selected from the one or more facial features of the fetus. The modified feature may cause pixel data of the image of the fetus to be enhanced or altered compared to the at least one image of the fetus as originally received. The AI-based imaging method further comprises rendering, on a display screen of a user computing device via an imaging application (app), the graphically enhanced image. The imaging app may be configured to execute on a user computing device, the user computing device comprising a device processor and a device memory. The imaging app may be communicatively coupled to the imaging server. The graphically enhanced image may depict the enhanced or altered pixel data.

In addition, as described herein, a tangible, non-transitory computer-readable medium storing instructions of an AI-based imaging system is disclosed. The instructions, when executed by one or more processors of an imaging server, may cause the one or more processors of the imaging server to receive at least one image of a fetus. The at least one image comprising pixel data of at least a portion of a face of the fetus. The instructions may further cause the one or more processors of the imaging server or one or more processors of a user computing device to generate, by an image enhancement AI model based on one or more facial features of the fetus, a graphically enhanced image of the fetus. The image enhancement AI model is trained with pixel data of a plurality of training images of fetuses. The image enhancement AI model configured to output respective graphically enhanced images of the fetuses, each graphically enhanced image having at least one image feature modified compared to an original image. The graphically enhanced image of the fetus comprises a new image with at least one modified feature selected from the one or more facial features of the fetus, the modified feature causing pixel data of the image of the fetus to be enhanced or altered compared to the at least one image of the fetus as originally received. Furthermore, the instructions may further cause the one or more processors of the imaging server or the one or more processors of the user computing device to render, on a display screen of a user computing device via an imaging application (app) configured to execute on a user computing device, the graphically enhanced image. The user computing device comprising a device processor and a device memory. The imaging app communicatively coupled to the imaging server. The graphically enhanced image depicting the enhanced or altered pixel data.

In accordance with the above, and with the disclosure herein, the present disclosure includes improvements in computer functionality or in improvements to other technologies at least because the claims recite that, e.g., generate, by an image enhancement model based on one or more facial features of a fetus, a graphically enhanced image of the fetus, wherein the graphically enhanced image of the fetus comprises a new image with at least one modified feature selected from the one or more facial features of the fetus. That is, the present disclosure describes improvements in the functioning of the computer itself or "any other technology or technical field" because e.g., a modified feature of one or more facial features of a fetus causes pixel data of the image of the fetus to be enhanced or altered compared to at least one image of the fetus as originally received. This improves over the prior art at least because the image enhancement model is trained with pixel data of a plurality of training images of fetuses, the image enhancement AI model configured to output respective graphically enhanced images of the fetuses. Additionally, this is an improvement over the prior because the image enhancement model may provide specific, customizable, and timely enhancements to an image of a fetus.

Advantages will become more apparent to those of ordinary skill in the art from the following description of the preferred embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive.

BRIEF DESCRIPTION OF THE DRAWINGS

The Figures described below depict various aspects of the system and methods disclosed therein. It should be understood that each Figure depicts an embodiment of a particular aspect of the disclosed system and methods, and that each of the Figures is intended to accord with a possible embodiment thereof. Further, wherever possible, the following description refers to the reference numerals included in the following Figures, in which features depicted in multiple Figures are designated with consistent reference numerals.

There are shown in the drawings arrangements which are presently discussed, it being understood, however, that the present embodiments are not limited to the precise arrangements and instrumentalities shown, wherein.

Figure 1:
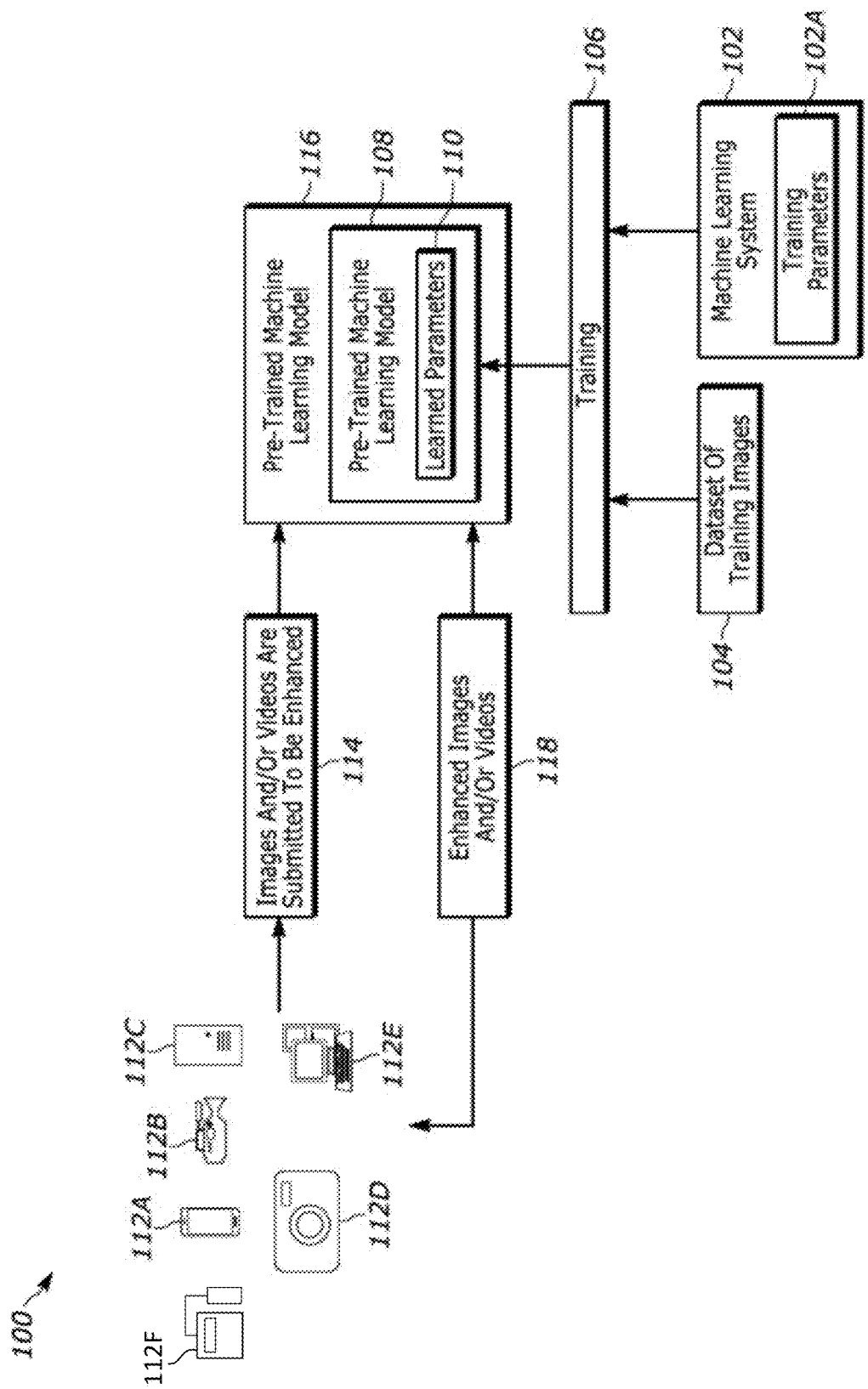
FIG. 1 illustrates a block diagram of the operation of an AI-based image enhancement system in accordance with various embodiments disclosed herein.

The Figures depict preferred embodiments for purposes of illustration only. Alternative embodiments of the systems and methods illustrated herein may be employed without departing from the principles of the invention described herein.

DETAILED DESCRIPTION

The present embodiments relate to, inter alia, generating an enhanced image and/or video of a fetus using an AI-based imaging system. Generally speaking, individuals (e.g., users, expectant parents, medical professionals) may seek to view an enhanced and/or lifelike image of a fetus. Individuals may do so with conventional techniques, such as 2D and/or 3D ultrasound images of a fetus; however, such images often lack clarity and visual appeal. The present invention rapidly and automatically improves one or more images of a fetus to appear more lifelike, clearer, and more visually appealing when compared to the previous state. The present invention enhances features and presentation to fit the desired standard of what is considered ideal. As a result, the present invention may, for example, provide medical professionals with clearer ultrasound images to interpret, and/or expectant parents with a more pleasurable ultrasound experience and/or stronger connection with their expected newborn, when compared to conventional techniques.

References to enhancing, improvement of physical appearance, shall be understood as any discernible alteration of the observable external attributes and characteristics of a fetus, including but not limited to changes in facial features and overall presentation, which, when objectively assessed, results in a more lifelike, aesthetically pleasing, or refined state compared to a prior condition or an established benchmark, and which may be achieved through various means, such as adjustments in contrast, lighting, texture, color, alterations to physical attributes by applying features (e.g., skin texture, wrinkles, eyelashes, eyebrows, fingernails, hair, nipples) and/or by altering features (e.g., clearer definition of noses, ears, fingers, lips, eyes), etc. The determination of an improved appearance is subject to the prevailing societal or professional standards. Accordingly, the techniques as described herein may be utilized to enhance an image according to the various societal and/or professional standards.

The AI model, also referred to herein as a machine learning (ML) model, of the imaging system may be capable of modifying a plurality of features in seconds. The AI model may, for example, adjust lighting, adjust colors, adjust skin tone, adjust lip color, adjust eyebrows, smoothen skin, etc. In some embodiments, features may comprise facial features. Additionally, or alternatively, features may comprise body features, such as chest, shoulders, arms, legs, hands, feet, fingers, toes, etc.

The enhancement process may be automatic; however, in some embodiments the user may select options to improve resolution, or specify a particular sex, race, gestational age, and/or attributes. A slider, button, dropdown, and/or other selection tool may be included to adjust the intensity in which features are changed. In some embodiments, these changes may be made using a tokenizer. A token is a piece of text which can be attached to training images, informing the ML Model of what the images represent. For example, an ML model trained with images attached with tokens "Asian" and "Male", may be able to reference these images if the user indicates the same token words.

In some embodiments, the process may utilize a diffuser deep learning model which can apply noise, known as forward diffusion, and reduce noise, known as reverse diffusion. In some embodiments the model is trained on target images using a U-Net model, which applies noise, as directed by training parameters, onto training images. By doing so, the model can predict noise on images and therefore how it should be applied. In practice, the now Pre-Trained ML Model may apply the predicted noise onto images, which to the user appears as an enhanced image.

In some embodiments, a masked autoencoder (MAE) technique may be utilized. MAEs are scalable self-supervised learners for computer vision. The MAE leverages the success of autoencoders for various imaging and natural language processing tasks. Some computer vision models may be trained using supervised learning, such as using humans to look at images and created labels for the images, so that the model could learn the patterns of those labels (e.g., a human annotator would assign a class label to an image or draw bounding boxes around objects in the image). In contrast, self-supervised learning may not use any human-created labels. One technique for self-supervised image processing training using an MAE is for before an image is input into an encoder transformer, a certain set of masks are applied to the image. Due to the masks, pixels are removed from the image and therefore the model is provided an incomplete image. At a high level, the model's task is to now learn what the full, original image looked like before the mask was applied.

In other words, MAE may include masking random patches of an input image and reconstructing the missing pixels. The MAE may be based on two core designs. First, an asymmetric encoder-decoder architecture, with an encoder that operates on the visible subset of patches (without mask tokens), along with a lightweight decoder that reconstructs the original image from the latent representation and mask tokens. Second, masking a high proportion of the input image, e.g., 75%, may yield a nontrivial and meaningful self-supervisory task. Coupling these two core designs enables training large models efficiently and effectively, thereby accelerating training (e.g., by 3× or more) and improving accuracy. MAE techniques may be scalable, enabling learning of high-capacity models that generalize well, e.g., a vanilla ViT-Huge model. As mentioned, the MAE may be effective in pre-training ViTs for natural image analysis. In some embodiments, the MAE uses the characteristic of redundancy of image information to observe partial images to reconstruct original images as a proxy task, and the encoder of the MAE may have the capability of deducing the content of the masked image area by aggregating context information. This contextual aggregation capability may be important in the field of image processing and analysis.

In some embodiments, LSTMs may be used with one or more various types of neural networks (e.g., convolutional neural networks (CNNs), deep neural network (DNNs), recurrent neural networks (RNNs), etc.). In some embodiments, CNNs, LSTM, and DNNs are complementary in their modeling capabilities and may be combined a unified architecture. For example, in such unified architecture, CNNs may be well-suited at reducing frequency variations, LSTMs may be well-suited at temporal modeling, and DNNs may be well-suited for mapping features to a more separable space. For example, input features to a ML model using LSTM techniques in the unified architecture may include segment features for each of a plurality of segments. To process the input features for each of the plurality of segments, the segment features for the segment may be processed using one or more CNN layers to generate first features for the segment; the first features may be processed using one or more LSTM layers to generate second features for the segment; and the second features may be processed using one or more fully connected neural network layers to generate third features for the segments, where the third features may be used for classification operations. In some examples, to process the first features using the one or more LSTM layers to generate the second features, the first features may be processed using a linear layer to generate reduced features having a reduced dimension from a dimension of the first features; and the reduced features may be processed using the one or more LSTM layers to generate the second features. Short-term features having a first number of contextual frames may be generated based on the input features, where features generated using the one or more CNN layers may include long-term features having a second number of contextual frames that are more than the first number of contextual frames of the short-term features. In some embodiments, the one or more CNN layers, the one or more LSTM layers, and the one or more fully connected neural network layers may have been jointly trained to determine trained values of parameters of the one or more CNN layers, the one or more LSTM layers, and the one or more fully connected neural network layers. In some embodiments, the input features may include log-mel features having multiple dimensions. The input features may include one or more contextual frames indicating a temporal context of a signal (e.g., input data). Advantageously, implementations for such unified architecture may leverage complementary advantages associated with each of a CNN, LSTM, and DNN. For example, convolutional layers may reduce spectral variation in input, which may help the modeling of LSTM layers. Having DNN layers after LSTM layers may help reduce variation in the hidden states of the LSTM layers. Training the unified architecture jointly may provide a better overall performance. Training in the unified architecture may also remove the need to have separate CNN, LSTM and DNN architectures, which may be expensive (e.g., in computational resource, in network traffic, in financial resources, in energy consumption, etc.). By adding multi-scale information into the unified architecture, information may be captured at different time scales.

In some embodiments, the process may utilize support vector machine learning techniques. In machine learning, support vector machines (SVMs) may be supervised learning models with associated learning algorithms that analyze data for classification and regression analysis. SVMs may be a robust prediction method, being based on statistical learning.

In some embodiments, the process may utilize K-nearest neighbors (KNN) techniques. KNN is a non-parametric classification method. In KNN classification, the output is a class membership. An object is classified by a plurality vote of its neighbors, with the object being assigned to the class most common among its k nearest neighbors (k is a positive integer, typically small). If k=1, then the object is assigned to the class of that single nearest neighbor. In KNN regression, the output is the property value for the object. This value is the average of the values of k nearest neighbors. KNN is a type of classification where the function is approximated locally and computation is deferred until function evaluation. Since this algorithm relies on distance for classification, if the features represent different physical units or come in vastly different scales then normalizing the training data can improve its accuracy dramatically.

In some embodiments, the process may utilize diffusion models (DM), otherwise called diffusion probabilistic models or score-based generative models. These models learn and operate by utilizing the latent structure of a dataset by modeling the way in which data points diffuse through the latent space. In the context of imaging, this means that a neural network is trained to denoise images blurred with Gaussian noise by learning to reverse the diffusion process. This consists of three major components: the forward process, the reverse process, and the sampling procedure. Three examples of generic diffusion modeling frameworks used in computer vision are denoising diffusion probabilistic models, noise conditioned score networks, and stochastic differential equations.

In some embodiments, the process may utilize Variational autoencoders (VAE). These are probabilistic generative models that may sometimes require a neural network operating with either encoder and/or decoder functions. An encoder neural network maps the input variable to a latent space that corresponds to the parameters of a variational distribution. The decoder has the opposite function, which is to map from the latent space to the input space, in order to produce or generate data points. Both networks are typically trained together with the usage of the reparameterization trick, although the variance of the noise model can be learned separately.

In some embodiments, the process may utilize latent variable models. This is a statistical model or probabilistic model that aims to explain observed data by introducing hidden or unobservable variables, often referred to as "latent variables." The observable data could be characterized as either continuous or categorical.

In some embodiments, the process may utilize U-Net models. These are a type of convolutional neural network (CNN) architecture commonly used for tasks related to image segmentation, which involves partitioning an image into different segments and assigning labels to each segment. The U-Net model has both a contracting path (the left side of the "U") and an expansive path (the right side of the "U"). The contracting path consists of convolutional and pooling layers that progressively reduce the spatial dimensions of the input image while increasing the number of feature channels. This path captures the contextual information from the input image. The expansive path involves a series of up-sampling and convolutional layers that gradually increase the spatial dimensions of the representation, allowing the network to generate a pixel-wise segmentation mask that aligns with the original input image's dimensions. Skip connections are a key feature of the U-Net architecture; they connect corresponding layers in the contracting and expansive paths. These connections allow the U-Net to combine high-resolution features from the contracting path with the up-sampled features from the expansive path, aiding in precise localization.

In some embodiments, the process may utilize written text, known as a "text encoder". This transforms textual input, such as sentences or paragraphs, into numerical representations that can be understood and processed by machine learning algorithms. These numerical representations capture the semantic and contextual information present in the text, enabling downstream tasks like sentiment analysis, machine translation, text classification, and more. Examples of text encoders commonly used are Bag-of-Words (BoW) and TF-IDF, Word Embeddings, Recurrent Neural Networks (RNNs), Long Short-Term Memory (LSTM) and Gated Recurrent Unit (GRU), and Transformer-based Models.

In some embodiments, a tokenizer in the context of natural language processing (NLP) may be utilized. The system comprises a processor configured to receive input text data and perform tokenization operations. Tokenization involves segmenting the input text data into discrete units referred to as tokens. These tokens are granular representations of textual content and can be configured to operate at various levels of linguistic analysis, including word-level, subword-level, or character-level tokenization. The tokenization process may incorporate preprocessing steps to ensure uniformity, such as lowercasing, punctuation removal, and handling of special characters. The system further comprises a set of predefined tokenization rules, which govern the treatment of linguistic elements within the input text data. These rules may encompass the handling of contractions, hyphenated words, punctuation, and other linguistic constructs. Additionally, the system may incorporate a designated vocabulary or token list, with tokens outside this vocabulary being managed through subword tokenization or categorized as unknown tokens. Special tokens may be introduced into the tokenized output, serving specific purposes depending on the application, such as classification or padding. Tokens may be used in training to attach particular attributes to training images, such as "Asian" and "Male". Users may utilize tokens in selecting parameters for image enhancement. Upon doing so, the Pre-Trained Machine Learning model will reference those tokens from its dataset of training images, influencing the outcome.

In some embodiments, the process may utilize noise to alter images. A common form is denoising, which refers to the process of removing unwanted or extraneous noise from a signal, data, image, or any form of information. Noise in this context refers to any unwanted variation or interference that can obscure the underlying structure or information contained within the data. Examples of noise are Gaussian noise, salt-and-pepper noise, speckle noise, shot noise, quantization noise, color noise, and aliasing noise. Denoising techniques could include mean and median filters, Gaussian filters, Non-local Means (NLM), Total variation denoising, wavelet denoising, and deep learning.

In some embodiments, a Generative Adversarial Network (GAN) may be used. The GAN system comprises two primary components: a generator and a discriminator, both implemented using deep neural networks. The generator is configured to receive random noise input and produce synthetic data samples that aim to mimic the distribution of a given dataset. The discriminator, in contrast, evaluates these generated samples alongside real data samples from the target distribution, discerning between real and synthetic data. The training process involves adversarial learning, wherein the generator strives to improve its output to fool the discriminator, while the discriminator aims to enhance its ability to distinguish between real and synthetic data. This adversarial feedback loop drives the iterative training process. In some embodiments, cGAN may be used, where the discriminator is instructed with additional conditions which must be fulfilled.

FIG. 1 shows an exemplary AI-based imaging system 100. As shown in FIG. 1, the AI-based imaging system may comprise a machine learning system 102 with a set of parameters 102A. In some embodiments, the machine learning system 102 may be a system configured to receive an input image, and generate an enhanced output image. The machine learning system 102 may learn values of the parameters 102A during a training stage 106 based on a dataset of training images 104. After the training stage 106, a trained machine learning system 108 is obtained that is configured with learned parameter values 110. The trained machine learning system 108 is used by the Pre-Trained Machine Learning Model 116 to enhance one or more images 114 captured by various imaging devices 112A-F. The image enhancement system 116 receives the image(s) 114 and outputs one or more enhanced images 118.

In some embodiments, an imaging server (e.g., image enhancement system 116) may receive at least one image of a fetus, the at least one image (e.g., one or ore images 114) captured by an imaging device (e.g., imaging devices 112A-F) and the at least one image comprising pixel data of at least a portion of a face of the fetus. Furthermore, the imaging server may generate, by an image enhancement AI model (e.g., trained machine learning system 108) based on one or more facial features of the fetus, a graphically enhanced image (e.g., one or more enhanced images 118) of the fetus, wherein the image enhancement AI model is trained with pixel data of a plurality of training images (e.g., dataset of training images 104) of fetuses, the image enhancement AI model configured to output respective graphically enhanced images of the fetuses, each graphically enhanced image having at least one image feature modified compared to an original image, and wherein the graphically enhanced image of the fetus comprises a new image with at least one modified feature selected from the one or more facial features of the fetus, the modified feature causing pixel data of the image of the fetus to be enhanced or altered compared to the at least one image of the fetus as originally received. Furthermore, the graphically enhanced image (e.g., one or more enhanced images 118) depicting the enhanced or altered pixel data may be rendered on a display screen of a user computing device (e.g., imaging devices 112A-F) via an imaging application (app) configured to execute on the user computing device, the user computing device comprising a device processor and a device memory, the imaging app communicatively coupled to the imaging server (e.g., image enhancement system 116).

In some embodiments, the machine learning system 102 may include a neural network with one or more parameters 102A. The neural network may be made up of multiple layers, each of which has one or more nodes. The parameters 102A of the neural network may be coefficients, weights, filters, or other types of parameters used by nodes in layers of the neural network. A node combines input data using the coefficients to generate an output value that is passed into an activation function of the node. The activation function generates an output value that is passed to the next layer of the neural network. The values generated by a final output layer of the neural network may be used to perform a task. In some embodiments, the final output layer of the neural network may be used to generate an enhanced version of an input image. For example, the values of the output layer may be used as inputs to a function for generating pixel values for an image that is to be output by the neural network. In some embodiments, the output layer of the neural network may comprise an enhanced version of the input image. For example, the output layer of the neural network may specify a value pixels of an enhanced version of the input image.

In some embodiments, the machine learning system 102 may include a convolutional neural network (CNN) such as a U-Net. The CNN may be made up of multiple layers of nodes. The parameters 102A may include filters that are applied at each layer of the CNN. Each layer of the CNN may be a set of one or more learnable filters with which an input to the layer in convolved. The results of the convolutions with each of the filter(s) are used to generate an output of the layer. The output of the layer may then be passed to a subsequent layer for another set of convolution operations to be performed by one or more filters of the subsequent layer. In some embodiments, the final output layer of the CNN may be used to generate an enhanced version of an input image. For example, the values of the output layer may be used as inputs to a function for generating pixel values for an image that is to be output by the neural network. In some embodiments, the output layer of the neural network may comprise an enhanced version of the input image. For example, the output layer of the CNN may specify a values for pixels of an enhanced image.

In some embodiments, the machine learning system 102 may implement one or more vision transformer (ViT) techniques. A ViT is a transformer-like model that handles vision processing tasks. While convolutional neural networks (CNNs) use convolution, a "local" operation bounded to a small neighborhood of an image, ViTs use self-attention, a "global" operation, since the ViT draws information from the whole image. This allows the ViT to capture distant semantic relevance in an image effectively. In some embodiments, the machine learning system 102 may include an artificial neural network (ANN). In some embodiments, the machine learning system 102 may include a recurrent neural network (RNN). In some embodiments, the machine learning system 102 may include a decision tree. In some embodiments, the machine learning system 102 may include a support vector machine (SVM). In some embodiments, the machine learning system may include genetic algorithms. Some embodiments are not limited to a particular type of machine learning model. In some embodiments, the machine learning system 102 may include a combination of one or more machine learning models. For example, the machine learning system 102 may include one or more neural networks, one or more decision trees, and/or one or more support vector machines.

In some embodiments, the training parameters 102A may include specifying the number of training steps used for each training image, setting the learning rate, setting the text encoder learning rate, the use of optimizers, the use of weight decay, and the use of tokenizers. The number of training steps indicates the number of times to reteach the same training image. The more training steps, the further reinforced the learning of these images are to the model. The learning rate indicates the step size in which the model is trained. A higher value means faster training, but may lead to suboptimal results. The text encoder learning rate operates the same, however for the text encoder portion of the model. Optimizers automatically update the training parameters during the training process, allowing for a more stable, reliable trained model. Weight decay improves generalization by introducing loss to the training processes. A higher weight loss provides more generalization, which may result in overgeneralization. Tokenizers allow text (tokens) to be tied to training images. In some embodiments, a plurality of training images of fetuses (e.g., dataset of training images 104) may include one or more images of fetuses with one or more target features. Target features, for example, may include any facial features congruent with the societal standard of what is considered ideal, as described elsewhere herein.

After the machine learning system is trained during the training stage 106, a trained machine learning system 108 is obtained. The trained machine learning system 108 may have learned parameters 110 that optimize performance of image enhancement performed by the machine learning system 108 based on the dataset of training images 104. The learned parameters 110 may include values of hyper-parameters of the machine learning system, values of coefficients or weights of the machine learning system, and values of other parameters of the machine learning system. Some parameters of the learned parameters 110 may be determined manually during the training stage 106, while others may be determined by automated training techniques performed during the training stage 106.

In some embodiments, the image enhancement system 116 uses the trained machine learning system 108 to perform image enhancement of one or more images 114 received from one or more imaging devices 112A-F. For example, the imaging device(s) may include a digital camera of a smart phone 112A, a camcorder 112B, an imaging device connected to a server 112C, a camera 112D, an imaging device connected to a personal computer system 112E, and an ultrasound imaging device 112F. Some embodiments are not limited to images from imaging devices described herein, as the machine learning system 108 may enhance images received from different imaging devices.

The image enhancement system 116 may receive the one or more images 114 as sonographic data. In some embodiments, sonographic data may comprise sonographic images of a fetus. The images may be two-dimensional (2D) and/or three-dimensional (3D) images obtained from an ultrasound imaging device (e.g., ultrasound imaging device 112F). The 2D images may be black-and-white images that depict the fetus, where the bones of the fetus are highlighted in white. The 3D images may be yellow/tan color images that depict specific features of the fetus in a well-defined formation, as shown in FIGS. 7A, 8A, and 9A. However, embodiments are not limited thereto, and the 2D and 3D images may include any other color schemes for identifying the bones and other features. Non-limiting examples of the size of sonographic images may comprise 1920×1080 pixels, 1280×872 pixels, 1280×720 pixels, 640×480 pixels, 852×480 pixels, or any other resolutions that the machine learning model may be able to process. Non-limiting examples of the format of sonographic images may comprise ".jpg", ".jpeg", ".gif", ".tiff", ".psd", ".raw", and others. In other embodiments, sonographic images may be printed on ultrasound thermal papers.

In other embodiments, sonographic data may comprise sonographic videos or cine clips of the fetus obtained from a four-dimensional (4D) ultrasound imaging device. Non-limiting examples of the resolution of videos or cine clips may comprise 1920×1080 pixels, 1280×872 pixels, 1280×720 pixels, 640×480 pixels, 852×480 pixels, or any other resolutions that the machine learning model may be able to process. Non-limiting examples of the format of sonographic images may comprise ".avi", ".mp4", ".mpeg", ".mkv", ".dcm", ".mov", ".wmv", ".flv", ".ts", and others. In some embodiments, videos or cine clips may be converted to a series of static images for the machine learning model to process. In other embodiments, sonographic data may comprise livestream of sonographic videos. The machine learning model (e.g., trained machine learning system 108) may process sonographic data directly transmitted from an ultrasound imaging device and generate a livestream of enhanced videos available for the expectant mother to watch in real time while she is under ultrasound examination.

The sonographic data, including sonographic images and videos, may be directly transmitted from an ultrasound imaging device (e.g., 112F). The machine learning model (e.g., trained machine learning system 108) may be implemented in an ultrasound imaging device such that the real-time sonographic images and videos obtain from the device may be used as input to the machine learning model for generating enhanced images and/or videos. The model may generate enhanced images and/or videos during ultrasound examination of an expectant mother. Alternatively, sonographic data may be stored in an imaging archiving system (e.g., picture archiving and communication system, PACS), web-based or cloud-based storage system. When the machine learning model accesses sonographic data, the model may generate enhanced images and/or videos.

The sonographic data may depict a fetus from an early gestational age to delivery of the newborn. In some embodiments, the sonographic data may depict a fetus from pregnancy weeks 8-41, 9-40, 10-39, 11-38, 12-37, 13-36, and the like.

The sonographic data may be pre-processed or augmented. In some embodiments, sections of images and videos that include personal information (e.g., personal health information (PHI) of expectant mother and fetus) may be removed or masked. In other embodiments, information associated health service to the fetus may be removed or masked, including information of the hospital and personnel who provided health care, and device information (e.g., device settings, scales, resolutions). The images and videos may be resized (e.g., downscaling, upscaling) preserving the original aspect of ratio or cropped. Other preprocessing steps may comprise perturbations to brightness, contrast, and color. The preprocessing may be performed by the machine learning model or other computing devices (including, but not limited to, the computing devices discussed herein).

The image enhancement system 116 uses the received image(s) 114 to generate inputs to the trained machine learning system 108. In some embodiments, the image enhancement system 116 may be configured to use pixel values of the image(s) 114 as inputs to one or more machine learning models (e.g., neural network(s)). In some embodiments, the image enhancement system 116 may be configured to divide the image(s) 114 into portions, and feed pixel values of each portion separately into the machine learning system 108 as inputs. In some embodiments, the received image(s) 114 may have values for multiple channels. For example, the received image(s) 114 may have a value for a red channel, green channel, and blue channel. These channels may also be referred to herein as "RGB channels."

After enhancing the received image(s) 114, the image enhancement system 116 outputs the enhanced image(s) 118. In some embodiments, the enhanced image(s) 118 may be output to a device from which the image(s) 114 were received. For example, the enhanced image(s) 118 may be output to mobile device 112A from which the image(s) 114 were received. The mobile device 112A may display the enhanced image(s) 118 in a display of the device 112A, and store the enhanced image(s) 118. In some embodiments, the image enhancement system 116 may be configured to store the generated enhanced image(s) 118. In some embodiments, the image enhancement system 116 may be configured to use the enhanced image(s) 118 for subsequent evaluation of performance of the image enhancement system 116 and/or retraining of the machine learning system 108.

In some embodiments, resolution of an image of a fetus (e.g., one or more images 114) may be enhanced or altered compared to the at least one image of the fetus as originally received.

In some embodiments, the image enhancement system 116 may be deployed on a device from which the image(s) 114 were received. For example, the image enhancement system 116 may be part of an application installed on the mobile device 112A that, when executed by the mobile device 112A, performs enhancement of the received image(s) 114. In some embodiments, the image enhancement system 116 may be implemented on one or more separate computers. The image enhancement system 116 may receive the image(s) 114 via a communication interface. The communication interface may be a wireless network connection, or a wired connection. For example, the image enhancement system 116 may be implemented on a server. The server may receive the image(s) 114 via a network (e.g., via the Internet). In another example, the image enhancement system 116 may be a desktop computer which receives the image(s) 114 via a wired connection (e.g., USB) from one or more of the devices 112A-F. Some embodiments are not limited by how the image enhancement system 116 obtains the image(s) 114.

In some embodiments, an imaging device (e.g., the one or more imaging devices 112A-F) may be communicatively coupled to an imaging server (e.g., the image enhancement system 116). In these embodiments, an image enhancement AI model (e.g., trained machine learning system 108) may receive, via a server processor (e.g., a processor (not shown) of the image enhancement system 116) or a device processor (e.g., a processor (not shown) of the one or more imaging devices 112A-F), at least one image of a fetus from the imaging device.

In some embodiments, a server processor (e.g., a processor (not shown) of the image enhancement system 116) or a device processor (e.g., a processor (not shown) of the one or more imaging devices 112A-F) may receive a second image (e.g., one or more images 114) of a second fetus, the second image captured by an imaging device (e.g., imaging devices 112A-112F), and the second image comprising pixel data of at least a portion of a face of the second fetus. Furthermore, an image enhancement AI model (e.g., trained machine learning system 108) may generate a second graphically enhanced image (e.g., one or more enhanced images 118) of the second fetus based on one or more facial features of the second fetus. The second graphically enhanced image of the second fetus may comprise a new second image with at least one modified feature selected from the one or more facial features of the second fetus, the modified feature causing pixel data of the second image of the second fetus to be enhanced or altered compared to the second image of the fetus as originally received. Furthermore, the second graphically enhanced image depicting the enhanced or altered pixel data may be rendered on a display screen of the user computing device (e.g., one or more imaging devices 112A-F).

In some embodiments, a server processor (e.g., a processor (not shown) of the image enhancement system 116) or a device processor (e.g., a processor (not shown) of the one or more imaging devices 112A-F) may receive at least one image (e.g., one or more images 114) of two or more fetuses comprising at least a first fetus and a second fetus, the at least one image of two or more fetuses captured by an imaging device (e.g., imaging devices 112A-112F), and the at least one image of two or more fetuses comprising pixel data of at least a portion of a face of the first fetus and at least a portion of a face of the second fetus. Furthermore, an image enhancement AI model (e.g., trained machine learning system 108) may generate a graphically enhanced image (e.g., one or more enhanced images 118) of the two or more fetuses based on one or more facial features of each of the two or more fetuses. The graphically enhanced image of the two or more fetuses may comprise a new image with at least one modified feature selected from the one or more facial features of each of the two or more fetuses, the modified feature causing pixel data of the image of the two or more fetuses to be enhanced or altered compared to the image of the two or more fetuses as originally received. Furthermore, the graphically enhanced image depicting the enhanced or altered pixel data may be rendered on a display screen of the user computing device (e.g., one or more imaging devices 112A-F).

In some embodiments, the dataset of training images 104 may comprise 2D and 3D sonographic images. In some embodiments, the training data may comprise sonographic videos or cine clips of the fetus. The fetus(es) depicted in the dataset of training images 104 may be from an early gestational age to delivery of the newborn. In some embodiments, the fetus may be from pregnancy weeks 8-41, 9-40, 10-39, 11-38, 12-37, 13-36, and the like. In some embodiments, the dataset of training images 104 may comprise sonographic images and videos collected from a variety of ultrasound imaging devices. The sonographic images and videos may be enhanced by a trained machine learning model or other image enhancement or editing tools (e.g., Photoshop).

In some embodiments, the dataset of training images 104 may comprise at least 50, at least 100, at least 150, at least 200, at least 500, at least 1000, at least 2,000, at least 3,000, at least 5,000, at least 8,000, at least 10,000, at least 12,000 sonographic images and/or videos. At least some of the sonographic images and/or videos may be enhanced by a trained machine learning model or other image enhancement or editing tools.

Figure 2:
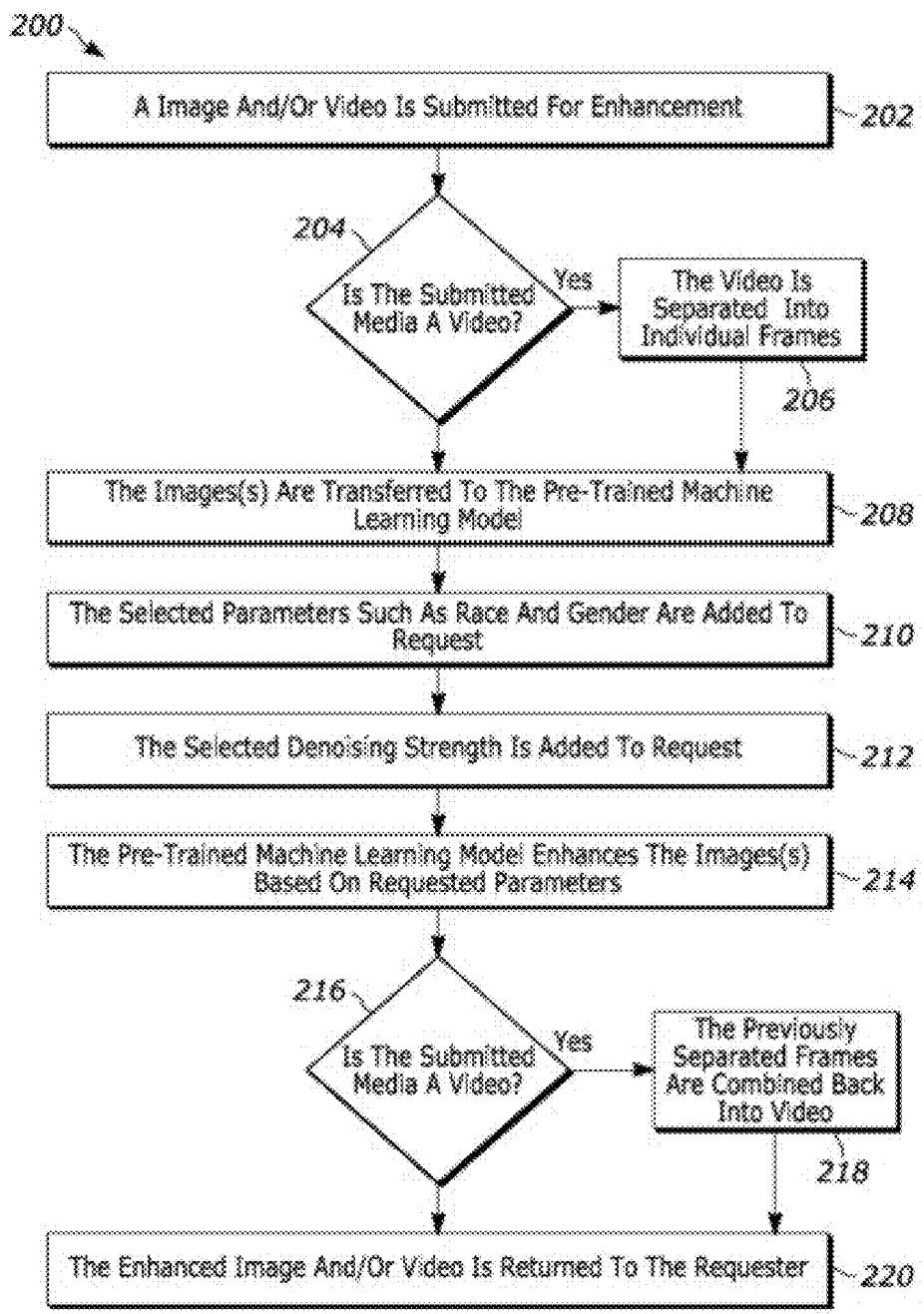
FIG. 2 illustrates a flow diagram for possible parameters with which the AI-based imaging system of FIG. 1 may operate, in accordance with various embodiments disclosed herein.

FIG. 2 shows the handling of prompts and videos by the machine learning system 200 which may be utilized in some embodiments. A user may upload an image and/or video 202 by means such as internet, wired connection, or direct storage transfer. Various image encoding formats could be used, such as JPG, PNG, JPEG, TIFF, BMP, SVG, GIF among others. Various video encoding formats may also be submitted, such as MP4, AVI, MOV, FLV, MKV, among others. In some embodiments, the machine learning system 200 may comprise obtaining an image and/or video by, e.g., an imaging app as described in FIG. 4.

The submitted media 202 is then determined to be either an image or video (block 204). This may be handled by the user device, server hosting the machine learning model, or a controller process between. If the submitted media 202 is a video, it is separated into individual frame images (block 206). These images may be in one of the aforementioned formats. In some embodiments, data unique to the video such as framerate and audio may be set aside.

Once the media is in image format, the image(s) are given to the Pre-Trained Machine Learning Model (block 208). The AI model may be hosted on the user's device, a 3rd party device, or on a server. Additional instructions may be provided to the AI in respect to physical attributes (block 210). For example, parameters regarding race, gender, or a particular style or appearance of a specific part of the face. These instructions could be provided from the user device, a 3rd party device, or a server.

The degree in which the fetus(es) physical appearance is modified is determined by the denoising strength, which is communicated to the AI model (block 214). There may be a default value, or it may be changed by the user, host, or 3rd party. A lower denoising strength results in less significant changes to the original input image, while a high denoising strength produces more significant changes to the original input image. In some embodiments, denoising strength may be adjusted by a slider, a drop-down menu, or directly inputted in a text box.

The Pre-Trained Learning Model then takes the aforementioned input image (block 202), parameters (block 210), and denoising strength (block 212), to output an enhanced version of the image (block 214). In some embodiments, the image is kept on the server, moved to a different server, or returned to the user.

If the original media 202 was a video (block 16), the frames are recombined into video format (block 218). In some embodiments, data from the original video such as framerate and audio would be applied back to the now enhanced video, if previously set aside.

The now enhanced image or video is returned to the user (block 220). In some embodiments, the media or copies of it could instead to kept on the server or sent to another device.

Figure 3:
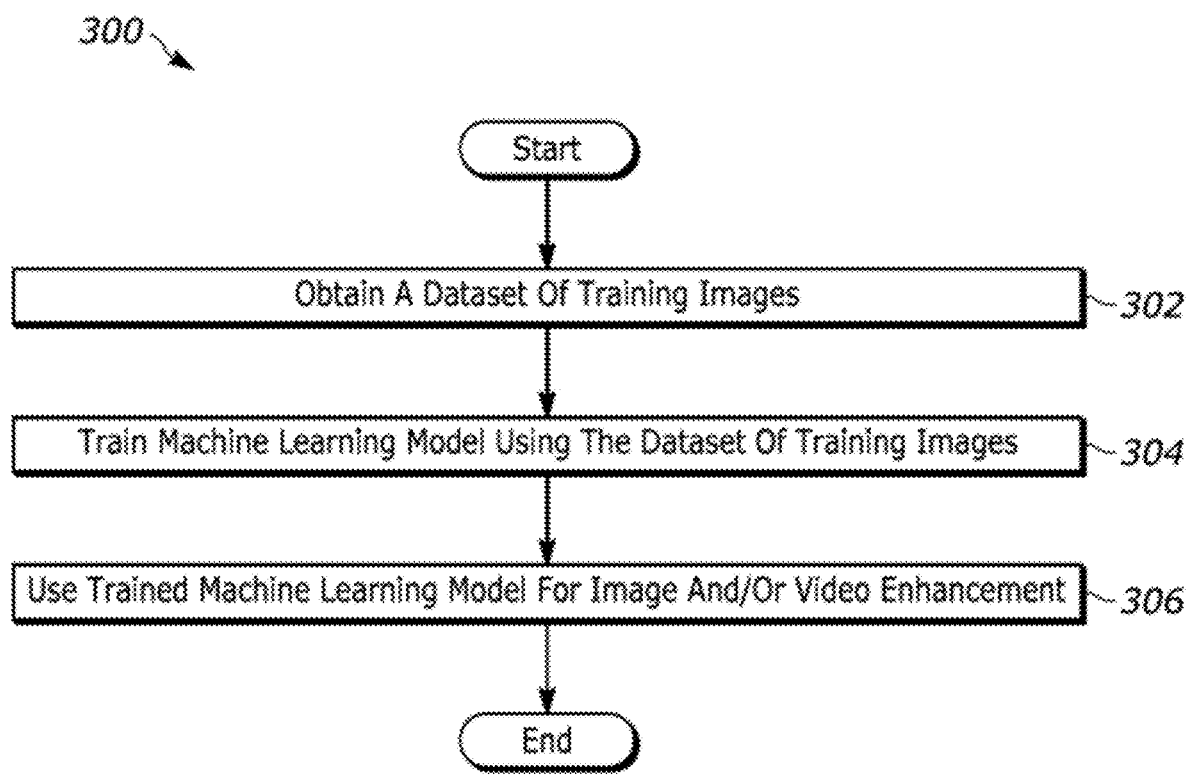
FIG. 3 illustrates a block diagram depicting a process for training a machine learning system in accordance with various embodiments disclosed herein.

FIG. 3 shows a process 300 for training a machine learning system, in accordance with some embodiments. Process 300 may be performed as part of training stage 106 described above with reference to FIG. 1. For example, process 300 may be performed to train machine learning system 102 with parameters 102A to obtain trained machine learning system 108 with learned parameters 110. Process 300 may be performed using any computing device(s) which include one or more hardware processors, as aspects of the technology are not limited in this respect.

Process 300 begins at block 302, where the system executing process 300 obtains a set of training images. The system may obtain training images that represent enhancement of images that are expected to be performed by the machine learning system. In some embodiments, the system may be configured to obtain a set of input images, and a corresponding set of output images. The output images provide a target enhanced outputs for the input images to be generated by a machine learning system that is being trained. In some embodiments, the input images may be images that represent fetus(es) with desired physical appearances. The output images may be corresponding output images that represent enhanced versions of the input images that have desired physical traits in the image. In some embodiments, training images may use tokenizers to define and categorize them. The system may obtain training images captured by one or more imaging devices, including ultrasound imaging devices, digital cameras, video recording devices, and/or the like, as described herein. For example, in some embodiments the images can be video frames, which can be processed using the techniques described herein. The system may be configured to receive the images via a wired connection, or wirelessly (e.g., via a network connection).

In some embodiments, the system may be configured to obtain training images that are captured using a specific device. In some embodiments, the system may be configured to obtain training images captured using a specific type of image sensor. For example, the system may receive training images that are captured from a particular type of imaging sensor (e.g., a specific model). The obtained images may then represent images that will be captured by an imaging device employing the particular type of imaging sensor. Accordingly, the machine learning system may be optimized for performance for the particular type of imaging sensor.

Figure 4:
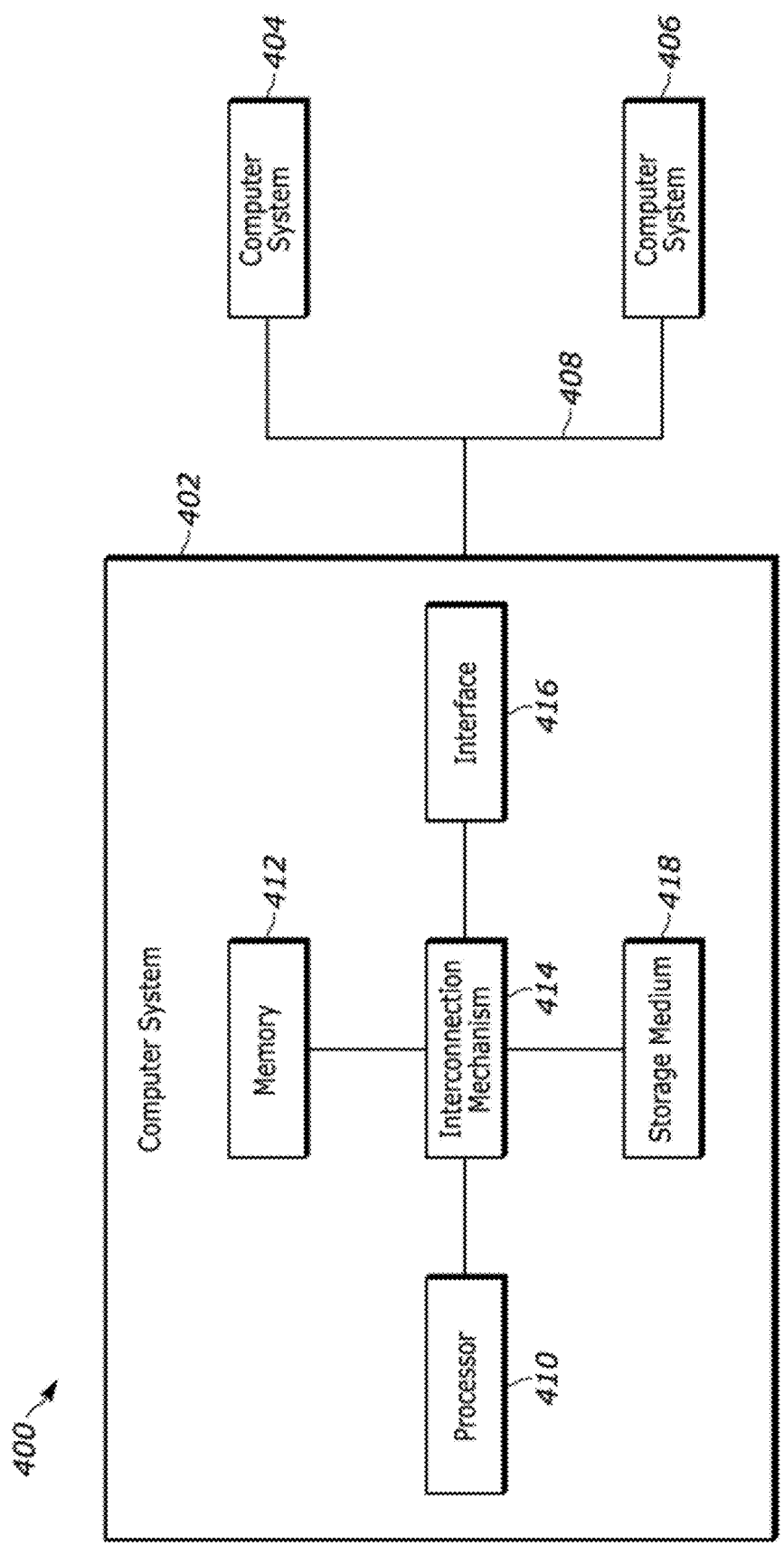
FIG. 4 illustrates an exemplary computer system, in which various aspects as described herein may be implemented in accordance with various embodiments disclosed herein.

In some embodiments, the act 302 may comprise obtaining, by a server processor (e.g., processor 410 as described in FIG. 4, processors (not shown) of image enhancement system 116 as described in FIG. 1) a plurality of training images of fetuses.

After obtaining the set of training images, process 300 proceeds to act 304 where the system trains the machine learning system using the obtained training images. In some embodiments, the system may be configured to perform automated supervised learning. In some embodiments, the system may be configured to perform the supervised learning to determine values of one or more parameters of the machine learning system.

In some embodiments, the act 304 may comprise training, by a server processor (e.g., processor 410 as described in FIG. 4, processors (not shown) of image enhancement system 116 as described in FIG. 1), an image enhancement AI model (e.g., trained machine learning system 108) by iteratively matching output of the image enhancement AI model with a ground truth label of at least one of the plurality of training images of fetuses, wherein the output of the image enhancement AI model is a graphically enhanced image of a fetus.

In some embodiments, the machine learning system may include one or more neural networks that are to be trained to perform image enhancement. In some embodiments, the machine learning system may include one or more convolution neural networks (CNNs). A convolution neural network performs a series of convolution operations for a given input image. The convolution operations are performed using one or more filters at each layer. The values to be used in the filters are to be determined during the training process. In some embodiments, the CNN may further include one or more layers with nodes that multiple inputs from a previous layer by respective weights, and then sum the products together to generate a value. The value may then be fed into an activation function to generate a node output. The values in the filters, and/or the values of the coefficients of the convolution neural network may be learned during the training process.

In some embodiments, the system may be configured to train parameters of the machine learning system by optimizing a loss function. The loss function may specify a difference (e.g., error) between an output generated by the machine learning system, and a target output. In some embodiments, the system may be configured to perform training to minimize the loss function for the obtained set of training images. Based on the value of a loss function calculated from an output of the machine learning system from an input image, the system may adjust one or more parameters of the machine learning system. In some embodiments, the system may be configured to use an optimization function to calculate adjustments to make to the parameter(s) of the machine learning system based on the value of a loss function. In some embodiments, the system may be configured to perform adjustments to parameters of the machine learning system until a threshold level of accuracy is reached for the testing images as indicted by the loss function. For example, the system may be configured to adjust the parameters during training until a minimum of the loss function is obtained for the training images. In some embodiments, the system may be configured to determine adjustments by a gradient descent algorithm. In some embodiments, the system may be configured to perform a batch gradient descent, stochastic gradient descent, and/or mini-batch gradient descent. In some embodiments, the system may be configured to use an adaptive learning rate in performing the gradient descent. For example, the system may be configured to use the RMSprop algorithm to implement the adaptive learning rate in the gradient descent.

In some embodiments, the system may be configured to use different and/or multiple loss functions. In some embodiments, the system may be configured to use a combination of multiple loss functions. For example, the system may be configured to use one or more of the mean absolute error (MAE), structure similarity (SSIM) index, color difference loss functions, and/or other loss functions (e.g., a loss function applied to bandpass images, as discussed in conjunction with FIG. 4). In some embodiments, the color difference may be calculated using Euclidean distance between pixels. In some embodiments, the color difference may be calculated using a delta-E 94 distance metric between pixels. Some embodiments are not limited to a particular color difference metric. In some embodiments, the system may be configured to apply the loss functions to one or more individual channels (e.g., red channel, green channel, blue channel).

In some embodiments, the system may be configured to use a linear combination of multiple loss functions. In some embodiments, the system may be configured to use a linear combination of MAE of one or more channels of the image, MAE of a filtered output, and SSIM. For example, the combination of multiple loss functions may be as shown in Equation 1 below.

$$\text{Error} = 1.6 * \text{MAE of red channel} + 1.0 * \text{MAE of green channel} + 1.6 * \text{MAE of blue channel} + 1.4 \text{SSIM} + 1.5 * \text{frequency filtered MAE}$$

In some embodiments, the system may be configured to set one or more hyper-parameters of the machine learning system. In some embodiments, the system may be configured to set values of the hyper-parameter(s) prior to initiating an automated training process. The hyper-parameters may include a number of layers in a neural network (also referred to herein as "network depth"), a kernel size of filters to be used by a CNN, a count of how many filters to use in a CNN, and/or stride length which specifies the size of steps to be taken in a convolution process. In some embodiments, the system may configure the machine learning system to employ batch normalization in which the outputs of each layer of the neural network are normalized prior to being input into a subsequent layer. For example, the outputs from a first layer may be normalized by subtracting a mean of the values generated at the first layer, and dividing each values by a standard deviation of the values. In some embodiments, the use of batch normalization may add trainable parameters to layers of a neural network. For example, the system may add a gamma and beta parameter that are used for normalization at each step. The machine learning system may subtract the beta value from each output of a layer, and then divide each output by the gamma value. In some embodiments, the neural network space can be compressed using quantization.

In some embodiments, the hyper-parameters of the machine learning system may be manually configured. In some embodiments, the hyper-parameters of the machine learning system may be automatically determined. For example, large scale computing techniques can be used to train models using different parameters, with the results stored into a shared storage. The shared storage can be queried to determine the best models, and in-turn to determine the best parameters (or range of values of parameters) in an automated fashion. In some embodiments, the system may be configured to store one or more values indicating performance associated with one or more hyper-parameter values. The system may be configured to automatically determine an adjustment to the hyper-parameter value(s) to improve performance of the system. In some embodiments, the system may be configured to store the value(s) indicating performance of the machine learning system when configured with respective hyper-parameter values in a database. The system may be configured to query the database for value(s) indicating performance of the machine learning system when configured with specific hyper-parameter values.

In some embodiments, the machine learning system may include a CNN. In some embodiments, the machine learning system may be configured to use a mix of depth-wise separable convolutions and full convolutions to reduce time required for the machine learning system to be trained, and to subsequently perform enhancement of images. In some embodiments, a mix of depth-wise separable convolutions and full convolutions may be used to reduce space required for the machine learning system. For example, to reduce the number of parameters of the machine learning system.

After training the machine learning system at block 304, process 300 proceeds to block 306 where the machine learning system is used for image enhancement. For example, the trained machine learning system may be used by image enhancement system 116 to perform enhancement of one or more received images. In some embodiments, the system 116 may be configured to obtain an image, and generate a corresponding light image according to the learned, and configured parameters of the machine learning system.

FIG. 4 shows a block diagram of a specially configured distributed computer system 400, in which various aspects may be implemented. As shown, the distributed computer system 400 includes one or more computer systems that exchange information. More specifically, the distributed computer system 400 includes computer systems 402, 404, and 406. As shown, the computer systems 402, 404, and 406 are interconnected by, and may exchange data through, a communication network 408. The network 408 may include any communication network through which computer systems may exchange data. To exchange data using the network 408, the computer systems 402, 404, and 406 and the network 408 may use various methods, protocols and standards, including, among others, Fiber Channel, Token Ring, Ethernet, Wireless Ethernet, Bluetooth, IP, IPV6, TCP/IP, UDP, DTN, HTTP, FTP, SNMP, SMS, MIMS, SS6, JSON, SOAP, CORBA, REST, and Web Services. To ensure data transfer is secure, the computer systems 402, 404, and 406 may transmit data via the network 408 using a variety of security measures including, for example, SSL or VPN technologies. While the distributed computer system 400 illustrates three networked computer systems, the distributed computer system 400 is not so limited and may include any number of computer systems and computing devices, networked using any medium and communication protocol.

As illustrated in FIG. 4, the computer system 402 includes a processor 410, a memory 412, an interconnection element 414, an interface 416 and data storage element 418. To implement at least some of the aspects, functions, and processes disclosed herein, the processor 410 may perform a series of instructions that result in manipulated data. The processor 410 may be any type of processor, multiprocessor, graphics processor, tensor processor, digital signal processor, or controller. Example processors may include a commercially available processor such as an Intel Xeon, Itanium, Core, Celeron, or Pentium processor; an AMD Opteron processor; an Apple A10 or A5 processor; a Sun UltraSPARC processor; an IBM Power5+ processor; an IBM mainframe chip; or a quantum computer. The processor 410 is connected to other system components, including one or more memory devices 412, by the interconnection element 414.

The memory 412 stores programs (e.g., sequences of instructions coded to be executable by the processor 410) and data during operation of the computer system 402. Thus, the memory 412 may be a relatively high performance, volatile, random access memory such as a dynamic random access memory ("DRAM") or static memory ("SRAM"). However, the memory 412 may include any device for storing data, such as a disk drive or other nonvolatile storage device. Various examples may organize the memory 412 into particularized and, in some cases, unique structures to perform the functions disclosed herein. These data structures may be sized and organized to store values for particular data and types of data.

Components of the computer system 402 are coupled by an interconnection element such as the interconnection mechanism 414. The interconnection element 414 may include any communication coupling between system components such as one or more physical busses in conformance with specialized or standard computing bus technologies such as IDE, SCSI, PCI and InfiniBand. The interconnection element 414 enables communications, including instructions and data, to be exchanged between system components of the computer system 402.

The computer system 402 also includes one or more interface devices 416 such as input devices, output devices and combination input/output devices. Interface devices may receive input or provide output. More particularly, output devices may render information for external presentation. Input devices may accept information from external sources. Examples of interface devices include keyboards, mouse devices, trackballs, microphones, touch screens, printing devices, display screens, speakers, network interface cards, etc. Interface devices allow the computer system 402 to exchange information and to communicate with external entities, such as users and other systems.

The data storage element 418 includes a computer readable and writeable nonvolatile, or non-transitory, data storage medium in which instructions are stored that define a program or other object that is executed by the processor 410. The data storage element 418 also may include information that is recorded, on or in, the medium, and that is processed by the processor 410 during execution of the program. More specifically, the information may be stored in one or more data structures specifically configured to conserve storage space or increase data exchange performance. The instructions may be persistently stored as encoded signals, and the instructions may cause the processor 410 to perform any of the functions described herein. The medium may, for example, be optical disk, magnetic disk or flash memory, among others. In operation, the processor 410 or some other controller causes data to be read from the nonvolatile recording medium into another memory, such as the memory 412, that allows for faster access to the information by the processor 410 than does the storage medium included in the data storage element 418. The memory may be located in the data storage element 418 or in the memory 412, however, the processor 410 manipulates the data within the memory, and then copies the data to the storage medium associated with the data storage element 418 after processing is completed. A variety of components may manage data movement between the storage medium and other memory elements and examples are not limited to particular data management components. Further, examples are not limited to a particular memory system or data storage system.

Although the computer system 402 is shown by way of example as one type of computer system upon which various aspects and functions may be practiced, aspects and functions are not limited to being implemented on the computer system 402 as shown in FIG. 4. Various aspects and functions may be practiced on one or more computers having a different architectures or components than that shown in FIG. 4. For instance, the computer system 402 may include specially programmed, special-purpose hardware, such as an application-specific integrated circuit ("ASIC") tailored to perform a particular operation disclosed herein. While another example may perform the same function using a grid of several general-purpose computing devices running MAC OS System X with Motorola PowerPC processors and several specialized computing devices running proprietary hardware and operating systems.

The computer system 402 may be a computer system including an operating system that manages at least a portion of the hardware elements included in the computer system 402. In some examples, a processor or controller, such as the processor 410, executes an operating system. Examples of a particular operating system that may be executed include a Windows-based operating system, such as, Windows NT, Windows 2000 (Windows ME), Windows XP, Windows Vista or Windows 8, 10, or 11 operating systems, available from the Microsoft Corporation, a MAC OS System X operating system or an iOS operating system available from Apple Computer, one of many Linux-based operating system distributions, for example, the Enterprise Linux operating system available from Red Hat Inc., a Solaris operating system available from Oracle Corporation, or a UNIX operating systems available from various sources. Many other operating systems may be used, and examples are not limited to any particular operating system.

The processor 410 and operating system together define a computer platform for which application programs in high-level programming languages are written. These component applications may be executable, intermediate, bytecode or interpreted code which communicates over a communication network, for example, the Internet, using a communication protocol, for example, TCP/IP. Similarly, aspects may be implemented using an object-oriented programming language, such as .Net, SmallTalk, Java, C++, Ada, C#(C-Sharp), Python, or JavaScript. Other object-oriented programming languages may also be used. Alternatively, functional, scripting, or logical programming languages may be used.

Additionally, various aspects and functions may be implemented in a non-programmed environment. For example, documents created in HTML, XML or other formats, when viewed in a window of a browser program, can render aspects of a graphical-user interface or perform other functions. Further, various examples may be implemented as programmed or non-programmed elements, or any combination thereof. For example, a web page may be implemented using HTML while a data object called from within the web page may be written in C++. Thus, the examples are not limited to a specific programming language and any suitable programming language could be used. Accordingly, the functional components disclosed herein may include a wide variety of elements (e.g., specialized hardware, executable code, data structures or objects) that are configured to perform the functions described herein.

In some examples, the components disclosed herein may read parameters that affect the functions performed by the components. These parameters may be physically stored in any form of suitable memory including volatile memory (such as RAM) or nonvolatile memory (such as a magnetic hard drive). In addition, the parameters may be logically stored in a propriety data structure (such as a database or file defined by a user space application) or in a commonly shared data structure (such as an application registry that is defined by an operating system). In addition, some examples provide for both system and user interfaces that allow external entities to modify the parameters and thereby configure the behavior of the components.

Based on the foregoing disclosure, it should be apparent to one of ordinary skill in the art that the embodiments disclosed herein are not limited to a particular computer system platform, processor, operating system, network, or communication protocol. Also, it should be apparent that the embodiments disclosed herein are not limited to a specific architecture.

Figure 5:
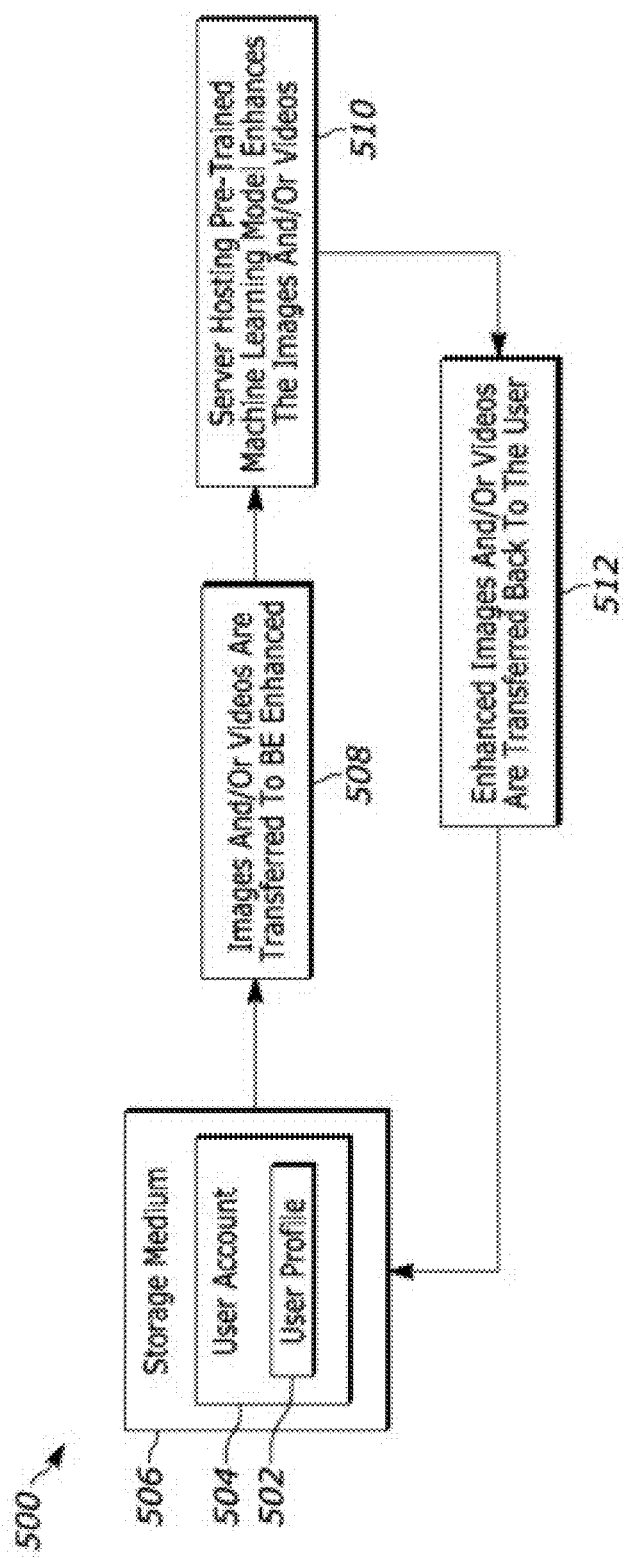
FIG. 5 illustrates a block diagram of the operation of an AI-based image enhancement system comprising an electronic health record profile of a user in accordance with various embodiments disclosed herein.

FIG. 5 shows an embodiment describing a possible format 500 of interaction between an electronic health record platform and the AI model. Images and/or videos are sent from the electronic health record profile 502. This profile is attached to the user's account 504, the data of which is saved in a storage medium, hosted on a server 506. The combination of these is called an electronic health record platform, examples of which are EPIC, CERNER, and MEDITECH.

Upon request from a user, a copy of the image and/or video is sent from the hosting storage medium 506 through a transfer mechanism such as internet, wired connection, or intermediary storage 508. If the AI model is hosted on the same server as the electronic health record account 504, this transfer is handled by an internal controller. The transferred media is then provided to the Pre-Trained Machine Learning Model to be enhanced 510. In some embodiments, additional parameters can be added to specify how the media is to be enhanced. It may also be upscaled or its resolution changed.

The enhanced media is then sent back to the user 512, often by the same means the original media was provided to the AI model. If there are other fetus(es) in the media, they may also send copies of the enhanced media.

In some embodiments, an electronic health record app may be configured to execute on a user computer device (e.g., the one or more imaging devices 112A-F of FIG. 1) and the electronic health record app may be communicatively coupled to an imaging server (e.g., the image enhancement system 116 of FIG. 1). In these embodiments, an image enhancement AI model (e.g., trained machine learning system 108) may receive, via a server processor (e.g., a processor (not shown) of the image enhancement system 116) or a device processor (e.g., a processor (not shown) of the one or more imaging devices 112A-F), at least one image of a fetus from the electronic health record app (e.g., as illustrated in act 508 of FIG. 5).

Figure 6:
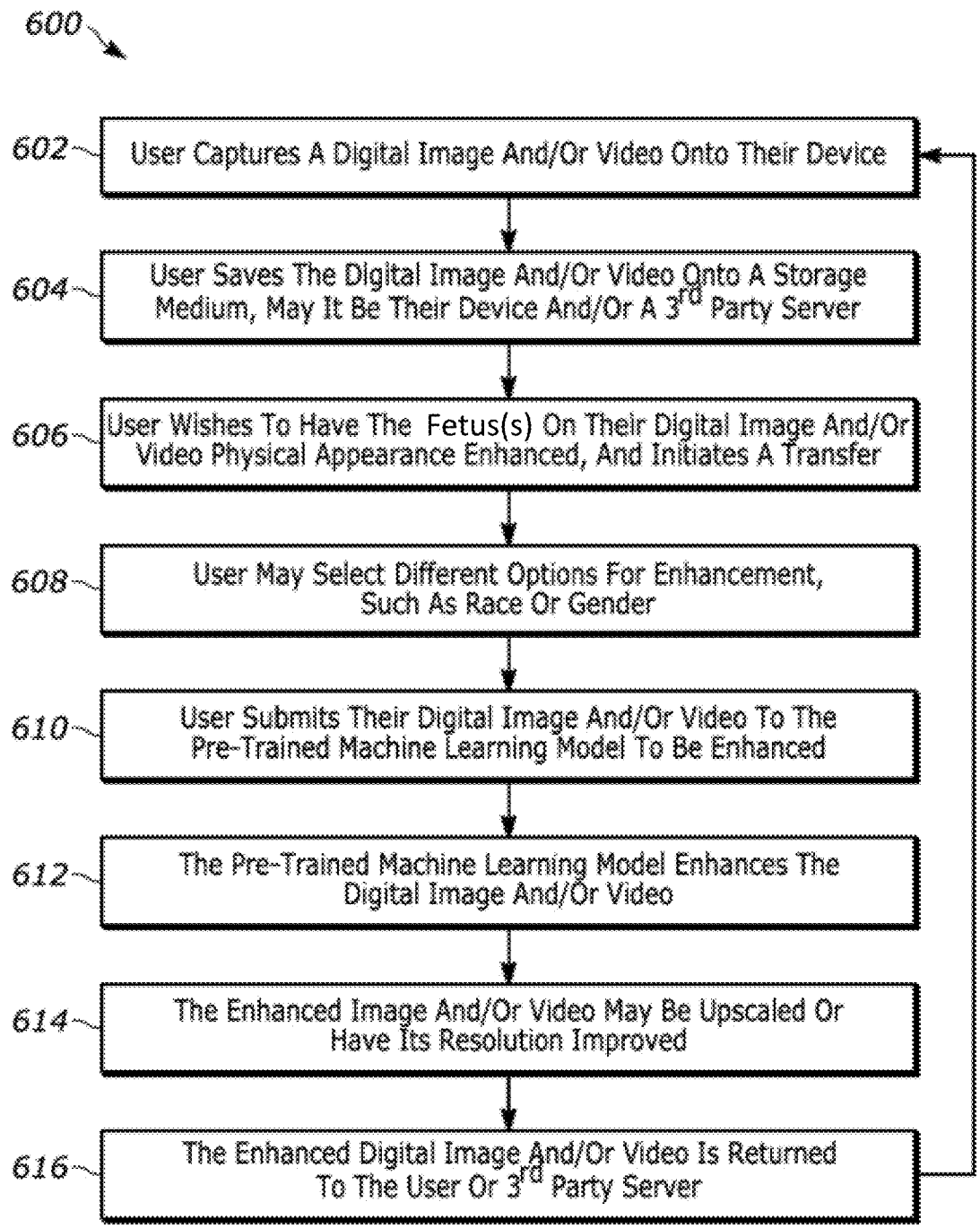
FIG. 6 illustrates a block diagram depicting an exemplary workflow implementation of the AI-based imaging system of FIG. 1 in accordance with various embodiments disclosed herein.

FIG. 6 shows an embodiment for a relationship between the user and the AI model 600. The process begins with the user capturing the image and/or video on a capture device (block 602). The form of this device may be a camera, cellular phone, camcorder, or any other device capable of capturing imaging data. The captured media is then stored onto a storage medium, such as the device itself or a 3rd party server (block 604). Should the user wish to enhance the fetus(es) captured within the image and/or video, they will initiate a transfer to the AI model (block 606). This transfer may take place via internet, wired connection, an intermediary storage medium, or within the user's own device.

In addition to the image and/or video submitted for enhancement, in some embodiments the user may have options to select different parameters such as race, gender, gestational age, or different types of attributes to apply to the fetus(es) within the image and/or video to be processed (block 608). In some embodiments, these prompts are tokenized. The media along with the prompts are submitted to the AI model (block 610). The AI model then enhances the media (block 612). Automatically, or as instructed by the user, the enhanced media may be changed to an indicated to a specific resolution or upscaled by AI (block 614) At this point, the AI has finished its work and the media is returned to the user (block 616).

In some embodiments, an imaging server (e.g., image enhancement system 116) may receive, via an imaging application (app), at least one tokenizer prompt; and generate, via a server processor (e.g., a processor (not shown) of the image enhancement system 116) or a device processor (e.g., a processor (not shown) of the one or more imaging devices 112A-F), a graphically enhanced image of a fetus based on the at least one tokenizer prompt.

FIGS. 7A, 8A, and 9A illustrate exemplary images of a fetus to be enhanced by the present invention. These images were downloaded from a server containing photos that are in the public domain. They were downloaded and stored into a storage medium within a personal computer. From there, they were submitted to a deep learning (DL) latent diffusion model (LDM) for future enhancement. The LDM loaded a Pre-Trained Machine Learning Model. This model was trained on images (e.g., dataset of training images 104 of FIG. 1) of racially diverse male and female fetus(es) and/or babies. Parameters using a tokenizer were also submitted to the LDM to change the target image. For FIG. 7A some of these tokens may be "Black" and "Woman". For FIG. 8A some of these tokens may be "Caucasian" and "Male". For FIG. 9A some of these tokens may be "Asian" and "Woman". These exemplary tokens reference training images used in training the Pre-Machine Learning Model. From these input tokens, the LDM may process the images, adjusting the noise on the submitted image (e.g., FIGS. 7A, 8A, 9A) to reflect the noise of the target image. To prevent the LDM from completely replicating the target image entirely and/or changing the appearance of the fetus(es) within the submitted media, the denoising strength was reduced to limit the amount of noise changed.

Figure 7B:
FIG. 7B illustrates an exemplary graphically enhanced image of the exemplary image of a fetus of FIG. 7A, the exemplary graphically enhanced image an output of the AI-based image enhancement system of FIG. 1 in accordance with various embodiments disclosed herein.
Figure 7A:
FIG. 7A illustrates an exemplary image of a fetus as received by the AI-based imaging system of FIG. 1 in accordance with various embodiments disclosed herein.
Figure 8B:
FIG. 8B illustrates an exemplary graphically enhanced image of the exemplary image of a fetus of FIG. 8A, the exemplary graphically enhanced image an output of the AI-based image enhancement system of FIG. 1 in accordance with various embodiments disclosed herein.
Figure 8A:
FIG. 8A illustrates an exemplary image of a fetus as received by the AI-based imaging system of FIG. 1 in accordance with various embodiments disclosed herein.
Figure 9B:
FIG. 9B illustrates an exemplary graphically enhanced image of the exemplary image of a fetus of FIG. 9A, the exemplary graphically enhanced image an output of the AI-based image enhancement system of FIG. 1 in accordance with various embodiments disclosed herein.
Figure 9A:
FIG. 9A illustrates an exemplary image of a fetus as received by the AI-based imaging system of FIG. 1 in accordance with various embodiments disclosed herein.

FIGS. 7B, 8B, and 9B illustrate exemplary graphically enhanced images of the respective exemplary images of a fetus illustrated in FIGS. 7A, 8A, and 9A. The exemplary graphically enhanced images correspond to the output of the LDM as previously described. The new and enhanced images generated resulted in the physical appearance of the original fetus(es) in the respective images and/or videos being improved. Subsequent to generation, the graphically enhanced images may be moved onto a storage medium for permanent storage and/or transmitted to the user computing device to be rendered for display to the user.

For example, the pixels and/or pixel data of any of FIGS. 7A, 8A, and 9A may be enhanced, modified, updated, positioned and/or repositioned, and/or replaced to generate the graphically enhanced images of FIGS. 7B, 8B, and 9B, respectively. Such pixel manipulation may be achieved by machine learning or artificial intelligence based systems and/or methods described herein.

ADDITIONAL CONSIDERATIONS

Although the disclosure herein sets forth a detailed description of numerous different embodiments, it should be understood that the legal scope of the description is defined by the words of the claims set forth at the end of this patent and equivalents. The detailed description is to be construed as exemplary only and does not describe every possible embodiment since describing every possible embodiment would be impractical. Numerous alternative embodiments may be implemented, using either current technology or technology developed after the filing date of this patent, which would still fall within the scope of the claims.

The following additional considerations apply to the foregoing discussion. Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules may provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and may operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location, while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other embodiments, the one or more processors or processor-implemented modules may be distributed across a number of geographic locations.

This detailed description is to be construed as exemplary only and does not describe every possible embodiment, as describing every possible embodiment would be impractical, if not impossible. A person of ordinary skill in the art may implement numerous alternate embodiments, using either current technology or technology developed after the filing date of this application.

Those of ordinary skill in the art will recognize that a wide variety of modifications, alterations, and combinations can be made with respect to the above described embodiments without departing from the scope of the invention, and that such modifications, alterations, and combinations are to be viewed as being within the ambit of the inventive concept.

This description of the exemplary embodiments is intended to be read in connection with the accompanying drawings, which are to be considered part of the entire written description.

The terms and words used in the following description and claims are not limited to the bibliographical meanings, but, are merely used to enable a clear and consistent understanding of the invention. Accordingly, it should be apparent to those skilled in the art that the following description of exemplary embodiments of the present invention is provided for illustration purpose only and not for the purpose of limiting the invention as defined by the appended claims and their equivalents.

It is to be understood that the singular forms "a," "an," and "the" include plural referents unless the context clearly dictates otherwise. Thus, for example, reference to "a component surface" includes reference to one or more of such surfaces unless the context clearly dictates otherwise.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

Certain inventive embodiments herein contemplate numerical ranges. When ranges are present, the ranges include the range endpoints. Additionally, every sub range and value within the range is present as if explicitly written out. The term "about" or "approximately" may mean within an acceptable error range for the particular value, which will depend in part on how the value is measured or determined, e.g., the limitations of the measurement system. For example, "about" may mean within 1 or more than 1 standard deviation, per the practice in the art. Alternatively, "about" may mean a range of up to 20%, up to 10%, up to 5%, or up to 1% of a given value. Where particular values are described in the application and claims, unless otherwise stated the term "about" meaning within an acceptable error range for the particular value may be assumed.

The patent claims at the end of this patent application are not intended to be construed under 35 U.S.C. § 112(f) unless traditional means-plus-function language is expressly recited, such as "means for" or "step for" language being explicitly recited in the claim(s). The systems and methods described herein are directed to an improvement to computer functionality, and improve the functioning of conventional computers.

What is claimed is:

1. An artificial intelligence (AI)-based imaging system for generating an enhanced image and/or video of a fetus, the AI-based imaging system comprising:

an imaging server comprising a server processor and a server memory;

an imaging application (app) configured to execute on a user computing device comprising a device processor and a device memory, the imaging app communicatively coupled to the imaging server; and an image enhancement AI model trained with pixel data of a plurality of training ultrasound images of fetuses, the image enhancement AI model configured to output respective graphically enhanced images of the fetuses, each graphically enhanced image having at least one pixel-based image feature of the fetus modified to generate a graphical enhancement comprising an enhanced physical appearance of the fetus compared to an original image generated with ultrasound;

wherein computing instructions are configured to execute on the server processor or the device processor to cause the server processor or the device processor to at least:

receive at least one ultrasound image of a fetus, the at least one image comprising pixel data of at least a portion of a face of the fetus as originally captured based on ultrasound, generate, by the image enhancement model based on one or more facial features of the fetus, a graphically enhanced image of the fetus, wherein the graphically enhanced image of the fetus comprises a new image with at least one modified feature selected from the one or more facial features of the fetus, the modified feature causing pixel data of the image of the fetus to be enhanced or altered to have an enhanced physical appearance of the fetus compared to the at least one image of the fetus as originally received; and render, on a display screen of the user computing device, the graphically enhanced image, the graphically enhanced image depicting the portion of a face of the fetus having the enhanced or altered pixel data.

2. The AI-based imaging system of claim 1, wherein the imaging app is further configured to execute on the device processor to cause the device processor to at least:

obtain the at least one image of the fetus, transmit, via the server processor or the device processor, the at least one image of the fetus to the image enhancement AI model, receive, via the server processor or the device processor, the graphically enhanced image of the fetus from the image enhancement AI model, and render, on the display screen of the user computing device, the graphically enhanced image.

3. The AI-based imaging system of claim 1, wherein the plurality of training images of fetuses include one or more images of fetuses with one or more target features.

4. The AI-based imaging system of claim 3, further comprising a training algorithm configured to execute on the server processor to cause the server processor to at least:

obtain the plurality of training images of fetuses, and train the image enhancement AI model by iteratively matching output of the image enhancement AI model with a ground truth label of at least one of the plurality of training images of fetuses, wherein the output of the image enhancement AI model is a graphically enhanced image of a fetus.

5. The AI-based imaging system of claim 1, further comprising an imaging device communicatively coupled to the imaging server, and wherein the image enhancement AI model receives, via the server processor or the device processor, the at least one image of a fetus from the imaging device.

6. The AI-based imaging system of claim 1, further comprising an electronic health record app configured to execute on the user computing device, the electronic health record app communicatively coupled to the imaging server, and wherein the image enhancement AI model receives, via the server processor or the device processor, the at least one image of a fetus from the electronic health record app.

7. The AI-based imaging system of claim 1, wherein resolution of the image of the fetus is enhanced or altered compared to the at least one image of the fetus as originally received.

8. The AI-based imaging system of claim 1, wherein the image enhancement AI model is further configured to execute on the server processor or the device processor to cause the server processor or the device processor to at least:

receive, via the imaging app, at least one tokenizer prompt; and generate a graphically enhanced image of the fetus based on the at least one tokenizer prompt.

9. The AI-based imaging system of claim 1, wherein the at least one image of the fetus comprises a first image of a first fetus, and wherein the computing instructions are further configured to execute on the server processor or the device processor to cause the server processor or the device processor to:

receive a second image of a second fetus, the second image comprising pixel data of at least a portion of a face of the second fetus, generate, by the image enhancement model based on one or more facial features of the second fetus, a second graphically enhanced image of the second fetus, wherein the second graphically enhanced image of the second fetus comprises a new second image with at least one modified feature selected from the one or more facial features of the second fetus, the modified feature causing pixel data of the second image of the second fetus to be enhanced or altered compared to the second image of the fetus as originally received; and render, on a display screen of the user computing device, the second graphically enhanced image, the second graphically enhanced image depicting the enhanced or altered pixel data.

10. The AI-based imaging system of claim 1, wherein the at least one image of the fetus comprises at least one image of two or more fetuses, and wherein the computing instructions are further configured to execute on the server processor or the device processor to cause the server processor or the device processor to:

receive at least one image of two or more fetuses, the two or more fetuses comprising at least a first fetus and a second fetus, the at least one image of two or more fetuses comprising pixel data of at least a portion of a face of the first fetus and at least a portion of a face of the second fetus, generate, by the image enhancement model based on one or more facial features of each of the two or more fetuses, a graphically enhanced image of the two or more fetuses, wherein the graphically enhanced image of the two or more fetuses comprises a new image with at least one modified feature selected from the one or more facial features of each of the two or more fetuses, the modified feature causing pixel data of the image of the two or more fetuses to be enhanced or altered compared to the at least one image of the two or more fetuses as originally received; and render, on a display screen of the user computing device, the graphically enhanced image, the graphically enhanced image depicting the enhanced or altered pixel data.

11. An artificial intelligence (AI)-based imaging method for generating an enhanced image and/or video of a fetus, the AI-based imaging method comprising:

receiving, at an imaging server comprising a server processor and a server memory, at least one ultrasound image of a fetus, the at least one image comprising pixel data of at least a portion of a face of the fetus as originally captured based on ultrasound;

generating, by an image enhancement AI model based on one or more facial features of the fetus, a graphically enhanced image of the fetus, wherein the image enhancement AI model is trained with pixel data of a plurality of training images of fetuses, the image enhancement AI model configured to output respective graphically enhanced images of the fetuses, each graphically enhanced image having at least one pixel-based image feature of the fetus modified to generate a graphical enhancement comprising an enhanced physical appearance of the fetus compared to an original image generated with ultrasound, and wherein the graphically enhanced image of the fetus comprises a new image with at least one modified feature selected from the one or more facial features of the fetus, the modified feature causing pixel data of the image of the fetus to be enhanced or altered to have an enhanced physical appearance of the fetus compared to the at least one image of the fetus as originally received; and rendering, on a display screen of a user computing device via an imaging application (app) configured to execute on a user computing device, the user computing device comprising a device processor and a device memory, the imaging app communicatively coupled to the imaging server, the graphically enhanced image, the graphically enhanced image depicting the portion of a face of the fetus having the enhanced or altered pixel data.

12. The AI-based imaging method of claim 11 further comprising:

obtaining, by the imaging app, the at least one image of the fetus;

transmitting, via the server processor or the device processor, the at least one image of the fetus to the image enhancement AI model;

receiving, via the server processor or the device processor, the graphically enhanced image of the fetus from the image enhancement AI model; and rendering, on the display screen of the user computing device, the graphically enhanced image.

13. The AI-based imaging method of claim 11, wherein the plurality of training images of fetuses includes one or more images of fetuses with one or more target features.

14. The AI-based imaging method of claim 13 further comprising:

obtaining, by the server processor, the plurality of training images of fetuses; and training, by the server processor, the image enhancement AI model by iteratively matching output of the image enhancement AI model with a ground truth label of at least one of the plurality of training images of fetuses, wherein the output of the image enhancement AI model is a graphically enhanced image of a fetus.

15. The AI-based imaging method of claim 11 further comprising:

receiving, at the image enhancement AI model, via the server processor or the device processor, the at least one image of a fetus from an imaging device communicatively coupled to the imaging server.

16. The AI-based imaging method of claim 11 further comprising:

receiving, at the image enhancement AI model, via the server processor or the device processor, the at least one image of a fetus from an electronic health record app configured to execute on the user computing device, the electronic health record app communicatively coupled to the imaging server.

17. The AI-based imaging method of claim 11, wherein resolution of the image of the fetus is enhanced or altered compared to the at least one image of the fetus as originally received.

18. The AI-based imaging method of claim 11, further comprising:

receiving, via the imaging app, at least one tokenizer prompt; and generating, via the server processor or the device processor, a graphically enhanced image of the fetus based on the at least one tokenizer prompt.

19. The AI-based imaging method of claim 11 further comprising:

receiving, via the server processor or the device processor, a second image of a second fetus, the second image comprising pixel data of at least a portion of a face of the second fetus, generating, by the image enhancement model based on the one or more facial features of the second fetus, via the server processor or the device processor, a second graphically enhanced image of the second fetus, wherein the second graphically enhanced image of the second fetus comprises a new second image with at least one modified feature selected from the one or more facial features of the second fetus, the modified feature causing pixel data of the second image of the second fetus to be enhanced or altered compared to the second image of the fetus as originally received; and rendering, on a display screen of the user computing device, the second graphically enhanced image, the second graphically enhanced image depicting the enhanced or altered pixel data.

20. The AI-based imaging method of claim 11 further comprising:

receiving, via the server processor or the device processor, at least one image of two or more fetuses, the two or more fetuses comprising at least a first fetus and a second fetus, the at least one image of two or more fetuses comprising pixel data of at least a portion of a face of the first fetus and at least a portion of a face of the second fetus, generating, by the image enhancement AI model based on the one or more facial features of each of the two or more fetuses, via the server processor or the device processor, a graphically enhanced image of the two or more fetuses, wherein the graphically enhanced image of the two or more fetuses comprises a new image with at least one modified feature selected from the one or more facial features of each of the two or more fetuses, the modified feature causing pixel data of the image of the two or more fetuses to be enhanced or altered compared to the at least one image of the two or more fetuses as originally received; and rendering, on a display screen of the user computing device, the graphically enhanced image, the graphically enhanced image depicting the enhanced or altered pixel data.

21. A tangible, non-transitory computer-readable medium storing instructions of an AI-based imaging system, that when executed by one or more processors of an imaging server cause the one or more processors of the imaging server to:

receive at least one ultrasound image of a fetus, the at least one image comprising pixel data of at least a portion of a face of the fetus as originally captured based on ultrasound; and when executed by the one or more processors of the imaging server or by one or more processors of a user computing device, the instructions further cause the one or more processors of the imaging server or the one or more processors of the user computing device to:

generate, by an image enhancement AI model based on one or more facial features of the fetus, a graphically enhanced image of the fetus, wherein the image enhancement AI model is trained with pixel data of a plurality of training images of fetuses, the image enhancement AI model configured to output respective graphically enhanced images of the fetuses, each graphically enhanced image having at least one pixel-based image feature of the fetus modified to generate a graphical enhancement comprising an enhanced physical appearance of the fetus compared to an original image generated with ultrasound, and wherein the graphically enhanced image of the fetus comprises a new image with at least one modified feature selected from the one or more facial features of the fetus, the modified feature causing pixel data of the image of the fetus to be enhanced or altered to have an enhanced physical appearance of the fetus compared to the at least one image of the fetus as originally received; and render, on a display screen of a user computing device via an imaging application (app) configured to execute on a user computing device, the user computing device comprising a device processor and a device memory, the imaging app communicatively coupled to the imaging server, the graphically enhanced image, the graphically enhanced image depicting the portion of a face of the fetus having the enhanced or altered pixel data.

\* \* \* \* \*